(12) United States Patent
Boyer et al.

(10) Patent No.: US 9,168,106 B2
(45) Date of Patent: Oct. 27, 2015

(54) DEVICE AND METHOD FOR INSTRUMENT ADJUSTMENT IN COMPUTER ASSISTED SURGERY

(75) Inventors: Anthony Boyer, Echirolles (FR); Stéphane Lavallee, St Martin D'Uriage (FR)

(73) Assignee: BLUE ORTHO, La Tronche (FR)

( * ) Notice: Subject to any disclaimer, the term of this patent is extended or adjusted under 35 U.S.C. 154(b) by 804 days.

(21) Appl. No.: 12/603,724

(22) Filed: Oct. 22, 2009

(65) Prior Publication Data
US 2010/0286710 A1    Nov. 11, 2010

Related U.S. Application Data

(60) Provisional application No. 61/175,556, filed on May 5, 2009.

(51) Int. Cl.
*A61B 19/00* (2006.01)
*A61B 17/15* (2006.01)
(Continued)

(52) U.S. Cl.
CPC ........... *A61B 19/5244* (2013.01); *A61B 17/155* (2013.01); *A61B 17/157* (2013.01);
(Continued)

(58) Field of Classification Search
CPC ............ A61B 2019/4857; A61B 17/808; A61B 17/8875; A61B 17/14; A61B 17/15; A61B 17/151; A61B 17/152; A61B 17/154; A61B 17/155; A61B 17/157; A61B 17/158; A61B 17/17; A61B 17/1703; A61B 17/1707; A61B 17/171; A61B 17/1717; A61B 17/1721; A61B 17/1725; A61B 17/1728; A61B 17/1739; A61B 17/175; A61B 17/1764; A61B 17/1767; A61B 17/80; A61B 2017/681

USPC ................ 606/53–54, 60, 65, 280, 79, 87–89
See application file for complete search history.

(56) References Cited

U.S. PATENT DOCUMENTS

| | | | |
|---|---|---|---|
| 4,669,359 | A | 6/1987 | Shiba |
| 4,681,843 | A | 7/1987 | Egerer et al. |

(Continued)

FOREIGN PATENT DOCUMENTS

| | | |
|---|---|---|
| DE | 10029737 | 5/2003 |
| EP | 0728446 | 8/1996 |

(Continued)

OTHER PUBLICATIONS

Amiot et al.; "Comparative Results Between Conventional and Computer-Assisted Pedicle Screw Installation in the Thoracic. Lumbar. and Sacral Spine"; Spine; 2000; vol. 25; No. 5; pp. 606-614.
(Continued)

*Primary Examiner* — Katherine Rodjom
*Assistant Examiner* — Kendra Obu
(74) *Attorney, Agent, or Firm* — Miles & Stockbridge P.C.

(57) ABSTRACT

The present invention relates to a device for adjusting the position of a surgical instrument (1) with respect to a solid (3) tracked by a navigation system (2), wherein the instrument (1) comprises a fixed part (11) that is rigidly fixed to the solid (3) and a mobile part (12) that is attached to the fixed part by screws (13), the device (4) comprising:
- a stem (41) comprising a tip (42) suited to the head (130) of the screws (13),
- a motorized system (45) for driving the stem (41) in rotation,
- a communication device with the navigation system (2), such that the navigation systems (2) transmits to the motorized system (45) the number of turns to apply to the stem (41) to reach the target position of each screw (13).

21 Claims, 9 Drawing Sheets

(51) Int. Cl.
  *A61B 17/88* (2006.01)
  *A61B 17/00* (2006.01)
(52) U.S. Cl.
  CPC ... *A61B17/8875* (2013.01); *A61B 2017/00026* (2013.01); *A61B 2017/00057* (2013.01); *A61B 2019/4857* (2013.01); *A61B 2019/5255* (2013.01); *A61B 2019/5483* (2013.01)

(56) References Cited

U.S. PATENT DOCUMENTS

| | | | |
|---|---|---|---|
| 4,706,665 A | | 11/1987 | Gouda |
| 4,800,325 A | | 1/1989 | Nakanishi |
| 4,813,312 A | * | 3/1989 | Wilhelm ............ 81/467 |
| 4,973,331 A | | 11/1990 | Pursley et al. |
| 5,010,263 A | * | 4/1991 | Murata ............ 310/68 B |
| 5,014,794 A | | 5/1991 | Hansson |
| 5,121,558 A | | 6/1992 | Caroe et al. |
| 5,806,518 A | | 9/1998 | Mittelstadt |
| 6,007,535 A | * | 12/1999 | Rayhack et al. ........ 606/57 |
| 6,172,824 B1 | | 1/2001 | Lehmann et al. |
| 6,554,837 B1 | * | 4/2003 | Hauri et al. .......... 606/87 |
| 6,712,824 B2 | | 3/2004 | Millard et al. |
| 7,126,628 B2 | | 10/2006 | Liu |
| 7,458,282 B1 | | 12/2008 | Wuester et al. |
| RE43,328 E | * | 4/2012 | Foley et al. .......... 600/429 |
| 2002/0095083 A1 | | 7/2002 | Cinquin et al. |
| 2002/0101465 A1 | | 8/2002 | Maeda |
| 2003/0181800 A1 | | 9/2003 | Bonutti |
| 2003/0222979 A1 | | 12/2003 | Liu |
| 2004/0003683 A1 | * | 1/2004 | Rudduck ............ 81/52 |
| 2004/0153083 A1 | | 8/2004 | Nemec et al. |
| 2004/0243207 A1 | * | 12/2004 | Olson et al. ........... 607/116 |
| 2005/0149038 A1 | * | 7/2005 | Haines et al. .......... 606/87 |
| 2005/0216032 A1 | * | 9/2005 | Hayden ............ 606/130 |
| 2005/0234466 A1 | | 10/2005 | Stallings |
| 2005/0257599 A1 | | 11/2005 | Kuo |
| 2006/0032554 A1 | | 2/2006 | Sprague et al. |
| 2006/0060092 A1 | | 3/2006 | Wu |
| 2006/0111726 A1 | * | 5/2006 | Felt et al. ............ 606/86 |
| 2006/0122617 A1 | * | 6/2006 | Lavallee et al. ......... 606/87 |
| 2006/0217733 A1 | * | 9/2006 | Plassky et al. ......... 606/87 |
| 2006/0235290 A1 | | 10/2006 | Gabriel et al. |
| 2007/0055289 A1 | | 3/2007 | Scouten et al. |
| 2007/0055389 A1 | | 3/2007 | Harwood |
| 2007/0085496 A1 | | 4/2007 | Philipp et al. |
| 2007/0225704 A1 | | 9/2007 | Ziran et al. |
| 2007/0233121 A1 | | 10/2007 | Carson |
| 2008/0140081 A1 | * | 6/2008 | Heavener et al. ........ 606/87 |
| 2008/0149582 A1 | | 6/2008 | Sluiter |
| 2011/0004199 A1 | | 1/2011 | Ross |
| 2011/0218546 A1 | * | 9/2011 | De la Fuente Klein et al. ............ 606/104 |

FOREIGN PATENT DOCUMENTS

| | | | |
|---|---|---|---|
| EP | 1444957 | | 8/2004 |
| EP | 1574170 | | 9/2005 |
| EP | 1665992 | | 6/2006 |
| EP | 1669033 A1 | * | 6/2006 |
| EP | 1679047 | | 7/2006 |
| JP | 2002134307 A | * | 5/2002 |
| WO | WO 01/78015 | | 10/2001 |
| WO | WO 02/37935 | | 5/2002 |
| WO | WO 03/009768 | | 2/2003 |
| WO | WO 2006100458 A2 | * | 9/2006 |
| WO | WO 2006106419 A2 | * | 10/2006 |
| WO | WO 2009/105479 | | 8/2009 |

OTHER PUBLICATIONS

Grotzner et al.; "Klinische Studie Zur Registrierungsfreien 3D-Navigation Mit OEM Mobilen C-Bogen Siremobil ISO-C 30, Electromedica"; 2003; 71(1):58-67.

Hamadeh et al.; "Automated 3-Dimensional Computed Tomographic and Fluoroscopic Image Registration"; 1998; Computer Aided Surgery; Biomedical Paper, vol. 3, pp. 11-19.

Horn; "Closed-Form Solution of Absolute Orientation Using Unit Quaternions"; 1987; Journal of the Optical Society of America A; vol. 4; p. 629-642.

International Preliminary Report on Patentability Based on International Application No. PCT/EP2009/063930 Issued Apr. 26, 2011.

International Search Report Based on PCT/EP2009/063930 Mailed Feb. 8, 2010.

Kosmopoulos et al.; "Pedicle Screw Placement Accuracy"; A Meta Analysis, Spine; 2007; 32(3): E111-20.

Laine et al.; "Accuracy of Pedicle Screw Insertion With and Without Computer Assistance: A Randomised Controlled Clinical Study in 100 Consecutive Patients"; European Spine Journal; 2000; 9(3):235-240.

Merloz et al.; "Computer Assisted Spine Surgery"; 1998; Computer Aided Surgery; vol. 3; pp. 297-305.

NN881 0457, IBM Technical Disclosure Bulletin, Oct. 1988.

NN881 0446, IBM Technical Disclosure Bulletin, Oct. 1988.

Schaeren et al; Effektive In-Vivo-Strahlendosis Bei Bildwandlerkrontollierter Pedikelinstrumentation vs. CT-Basierter Navigation; Orthopade; Apr. 2002; 31(4):392-396.

Sukovich et al; "Miniature Robotic Guidance for Pedicle Screw Placement in Posterior Spinal Fusion: Early Clinical Experience With the Spineassist"; International Journal of Medical Robotics and Computer Assisted Surgery; Jun. 2006; 2(2):114-22.

Susil et al.; "A Single Image Registration Method for CT Guided Interventions" MICCAI'99; Springer-Verlag Berlin Heidelberg (1999); LNCS 1679; pp. 798-808.

Wendl et al; "ISO-C3D-Gestutzte Navigerte Implantation Von Pedkiel-Schrauben an BWS UNO LWS"; Unfallchirurg; Nov. 2003; 106(11):907-913.

* cited by examiner

DEVICE AND METHOD FOR INSTRUMENT ADJUSTMENT IN COMPUTER ASSISTED SURGERY

PURPOSE OF THE INVENTION

The present invention relates to a device and a method that allow adjusting a surgical Instrument position more accurately and faster than with a conventional method. The scope of the invention is any surgical Instrument where the Instrument position is adjustable by screws, and tracked in real-time by a navigation system. The invention is an intraoperative surgical Device.

BACKGROUND OF THE INVENTION

It is known that some navigation systems are tracking instrument position during their position adjustment.

It is known that some instruments are adjusted by screws, such as cutting planes of cutting blocks for total knee replacement procedures.

Many devices use screws to adjust and finely tune the position of a surgical instrument. For instance, in U.S. Pat. No. 6,712,824, Millar uses a mechanism with three screws to adjust the plane position of a cutting guide for knee surgery, but the screws must be adjusted manually which takes time. Similar principles can be found in EP 1 444 957 by Cusick, or US 2006/0235290 by Gabriel. Moreover the mechanical architecture in those inventions is serial and it does not lock automatically to a given position when the screws are not turned, it is therefore necessary to lock the screws to a given position with an additional locking screw mechanism or to use additional pins in the bone to fix the cutting guide.

More complex architectures are using more than three screws in order to adjust cutting blocks. For instance, in EP 1 669 033, Lavallee uses a navigation system to adjust the position of several screws of a femoral cutting block but this process is not easy and it takes a long time.

The tracking technology of trackers and navigation systems is independent of the invention, provided that the trackers are tracked in real-time by the navigation system. It includes, but is not limited to optical active technology, with active infrared Light Emitting Diodes (LEDs) on trackers, optical passive technology (with passive retro-reflective markers on trackers), mechanical passive arms with encoders, accelerometers and gyrometers, or magnetic technology. Those tracking technologies are known as prior art of navigation systems for surgery.

Referring to FIG. 1, the instrument 1 is any surgical instrument that has the following characteristics:

[A] The instrument 1 has a tracker 10 attached thereon so that it is tracked by the navigation system 2. The navigation system 2 comprises a camera 20 and a computer 21 with a screen.

[B] The instrument 1 is rigidly fixed to a solid 3 that is also tracked by the navigation system 2.

[C] The instrument has a fixed part 11 which is fixed to the solid 3 and a mobile part 12 which is mobile with respect to the fixed part 11.

[D] The position of the fixed part 11 with respect to the mobile part 12 can be adjusted by screws 13. The number of screws is independent of the invention.

A screwdriver 7 is used to adjust the instrument position with respect to the solid 3 in a target position. The target position of the instrument is supposed to be selected by the surgeon or set to default values with respect to anatomical landmarks digitized with the navigation system. The target position is represented by a geometric relationship between the fixed part 11 of the instrument and its mobile part 12. By trivial calibration, the target position can be represented equivalently to a geometric relationship between a tracker attached to the mobile part and a tracker attached to the fixed part or to the solid.

The problem is for the user to move several screws 13 independently to move the mobile part 12 until the geometric relationship between the mobile part tracker 10 and the solid tracker 30 matches within a very low tolerance limit such as for instance 0.5 mm and 0.2°.

The manual adjustment of individual screws 13 takes a long time and it is difficult to converge towards a solution.

To help this process, for any initial position of the screws 13 and mobile part 12, the computer 21 of the navigation system 2 can calculate the necessary screw differential adjustments $DS_i$, for each screw $13i$ (where i is from 1 to N and N is the number of screws), which is necessary to bring the mobile part 12 in the target position. This is an easy calculation that only requires knowing the geometry of the screw placements with respect to the mobile and fixed parts and that is specific to each geometry. In a first step, the display of the navigation system can simply show the adjustments necessary $DS_i$ on each screw to the user such that the user follows the indications on the screen. While the screws 13 are manually adjusted, the values $DS_i$ are recalculated in real-time and the user can adjust the various screws accordingly.

However, this process remains long and complicated.

The present invention thus aims at providing an adjustment process that is short and simple in order to save intraoperative time.

BRIEF DESCRIPTION OF THE INVENTION

In order to make this process really fast and simple, the invention proposes to use a device which communicates with the computer such that placing the device in contact with the screws and using one of the automatic screw detection methods described below can generate an automated motion of the device to match the desired adjustment $DS_i$.

One object of the invention is a device for adjusting the position of a surgical instrument with respect to a solid tracked by a navigation system, wherein the instrument comprises a fixed part that is rigidly fixed to the solid and a mobile part that is attached to the fixed part by screws, said device comprising:

a stem comprising a tip suited to the head of the screws, a motorized system for driving said stem in rotation, communication means with the navigation system, such that the navigation systems transmits to the motorized system the number of turns to apply to the stem to reach the target position of each screw.

For each adjustment screws of the instrument, the navigation system computes the number of turns and the rotation direction that needs to be applied. Then, by inserting the tip of the device in the screw's head and by pressing a button to activate the device, the motorized device turns automatically the screw until the screw reaches the target position. By applying this process for each adjustment screw, the instrument is adjusted more precisely and faster than with the conventional mechanical ancillaries or with existing navigation systems.

Advantageously, the device further comprises detection means for identifying which screw the tip of the device is in contact with, and the communication means of the device are able to transmit said identification information to the navigation system.

According to an embodiment of the invention, said detection means comprise a sliding stem able to slide inside the stem and a position sensor adapted to measure the displacement of the sliding stem with respect to the tip of the device.

According to another embodiment, the detection means comprise electrical connectors arranged at the tip of the device and an ohmmeter.

According to another embodiment, the detection means comprise a "Hall effect" sensor arranged in the tip of the device.

According to another embodiment, the detection means comprise an optical sensor, a first optical fiber and a second optical fiber, the first and second optical fibers being arranged inside the stem so as to respectively light the cavity of the screw head and bring the reflected light to said optical sensor.

According to another embodiment, the detection means comprise a tracker rigidly attached to the device.

Another object of the invention is a method of adjusting the position of a surgical instrument with respect to a solid tracked by a navigation system, wherein the instrument comprises a fixed part that is rigidly fixed to the solid and a mobile part that is attached to the fixed part by screws, comprising the following steps:

determining the position of the mobile part of the instrument with respect to the solid, comparing said determined position with respect to a target position, if said determined position is different from the target position, computing, for each screw of the instrument, the number of turns to apply in order to reach said target position, positioning the tip of the device as described above in each screw head, operating the motorized system of the device such that it applies to the stem the computed number of turns.

Another object of the invention is the device described above for use in a method comprising the steps of determining the position of the mobile part of the instrument with respect to the solid, comparing said determined position with respect to a target position, if said determined position is different from the target position, computing, for each screw of the instrument, the number of turns to apply in order to reach said target position, positioning the tip of the device as described above in each screw head, operating the motorized system of the device such that it applies to the stem the computed number of turns.

Another object of the invention is a computer assisted surgical navigation system for adjusting the position of a surgical instrument computer assisted surgical navigation system for adjusting the position of a surgical instrument with respect to a solid, wherein the instrument comprises a fixed part that is rigidly fixed to the solid and a mobile part that is attached to the fixed parts by screws, the system comprising:

a first reference element applied to the solid that generates a first three-dimensional dynamic reference tracker, which is independently registered in the navigation system a second reference element applied to mobile part of the surgical instrument that needs to be adjusted, that generates a second three-dimensional dynamic reference tracker, which is independently registered in the navigation system the device as described above wherein the number of turns and the rotation direction are determined for each screw by the navigation system, taking into account the current mobile part position, the target mobile part position, the design of the screws and the design of the instrument, and transmitted to the device by the communication means.

DESCRIPTION

The invention can be used for adjusting one planar instrument with three screws, or a linear guide with four screws, or a cutting block sliding on a planar surface with 2 screws, or a complete solid with at least six screws. Those numbers of screws relate to the number of degrees of freedom for each geometrical type of adjustable Instrument or guide.

Figure 1:
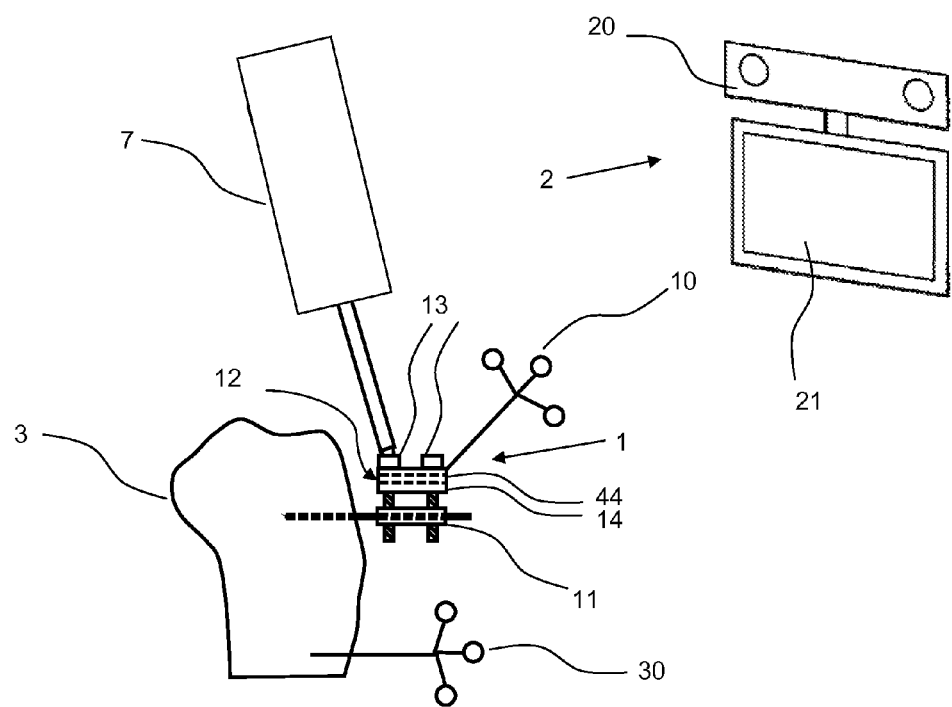
FIG. 1 is a sequential view showing a conventional screwdriver positioned into the screws of the instrument.

The device and navigation system used in the present invention are similar to those presented in FIG. 1. However, the device according to the invention is different from the conventional screwdriver and is illustrated on FIGS. 2 to 8.

In one preferred embodiment, the surgical application is the total replacement of the knee joint; the solid 3 is the patient's tibia or the basis of the instrument fixed to the tibia, and the tracker 30, rigidly fixed to the bone, allows the navigation system 2 to track the tibia; the instrument 1 is a cutting block on which a cutting plane 14 must be aligned with the desired target plane selected by the surgeon; the instrument mobile part position is adjustable by three screws; the position of the three screws determine a unique position of the cutting block with respect to the fixed part 11. The cutting plane position is defined by a slope angle, a varus/valgus angle, and a cut thickness with respect to the tibia. The target position is entered into the navigation system by the surgeon or set to default values with respect to anatomical landmarks digitized by the surgeon with the navigation system. The goal of the device is then to adjust the position of the cutting block in the target position.

In one preferred embodiment, the surgical application is the total replacement of the knee joint; the solid 3 is the patient's femur or the basis of the instrument fixed to the femur, and the solid tracker 30, rigidly fixed to the bone, allows the navigation system 2 to track the femur; the instrument 1 is a cutting block on which a cutting plane 14 must be aligned with the desired target plane selected by the surgeon; the Instrument Mobile Part position is adjustable by three screws; the position of the three screws determine a unique position of the cutting block with respect to the fixed part 11. The plane position is defined by a slope angle, a varus/valgus angle, and a cut thickness with respect to the femur. The target position is entered into the navigation system by the surgeon or set to default values with respect to anatomical landmarks digitized by the surgeon with the navigation system. The goal of the device is then to adjust the position of the cutting block in the target position.

Device

Figure 2:
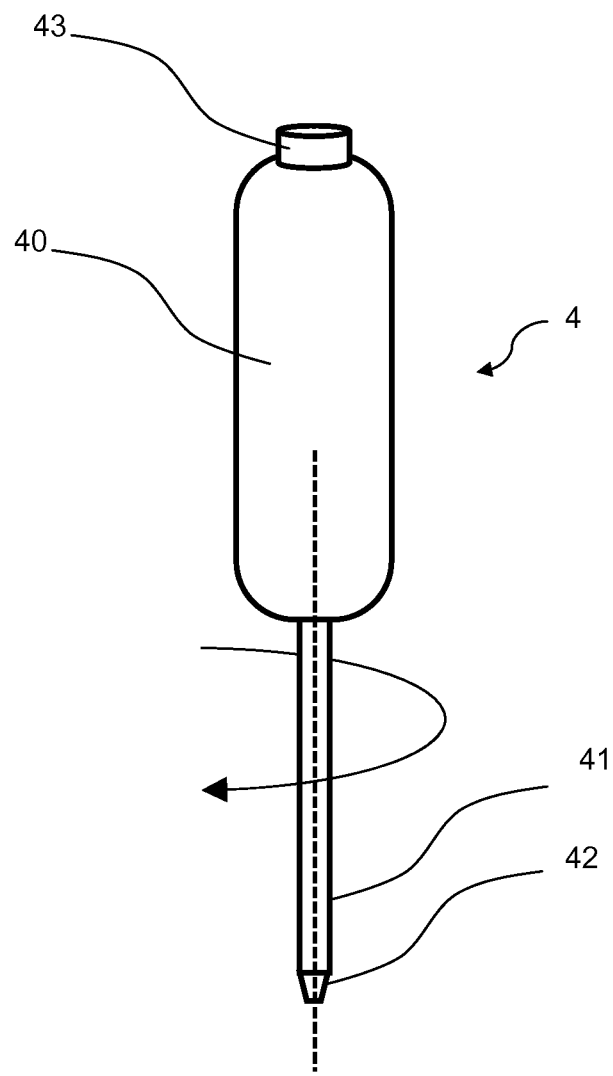
FIG. 2 is an elevational view of the device according to the invention.

As represented on FIG. 2, the device 4 according to the invention is a motorized screwdriver that comprises a body or handle 40, a stem 41, a tip 42, an optional button 43 that is activated by the user, and an encapsulated battery that brings enough power to rotate the screwdriver.

Figure 3:
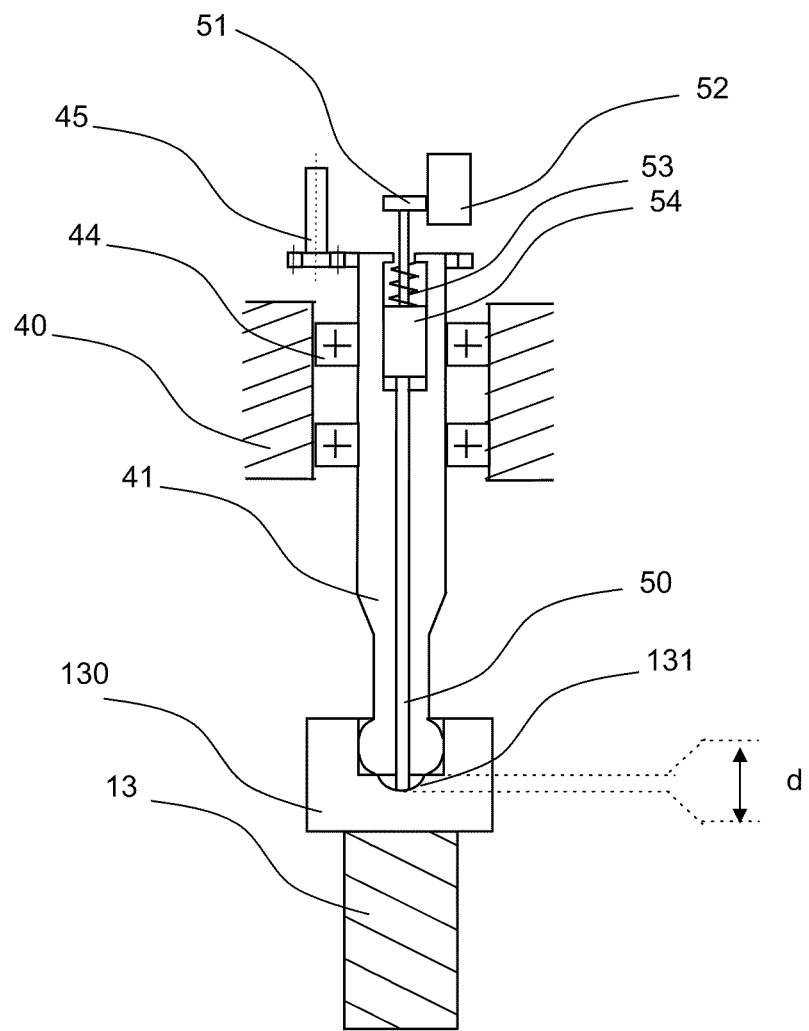
FIG. 3 is a partial sectional view of the device stem, device tip, and instrument screws, where the auto-detection of the screw is done by a mechanical solution.

As better seen on FIG. 3, the stem 41 is rotating with respect to the device body 40 thanks to a rolling system 44. The rotation is controlled by a motorized system 45. It must be noted that the devices illustrated on FIGS. 4 to 7 also comprise said rolling and motorized systems, although these features are not shown on these figures. Usually, a reduction ratio is used between the motor and the stem using standard gears so that one turn of the motor makes only 1/50 turn of the stem, which improves the stability and accuracy of the system.

The device is controlled by the computer 21 of the navigation system. The controlled parameters are: turn direction, number of turns, turn speed and turn acceleration. The number of turns and the direction are parameters given by the computer and transmitted through the wireless protocol to the device.

The device communicates with the computer through a wireless protocol, such as WIFI® or BLUETOOTH® or ZIG-BEE®. In one preferred embodiment, the wireless communication is based on the Bluetooth communication protocol. Optionally, the communication can be also performed by standard wires with a standard wire and communication protocol such as USB®, ETHERNET®, IEEE 1394, RS232, or a proprietary wire and communication protocol, and in that case the power supply is also brought by a cable.

In a simple embodiment of the invention, the computer display indicates to the user the screw in which the screwdriver must be placed. When the user has placed the screwdriver in the head of the screw indicated on the screen, the user presses a button and the screwdriver moves the screw to the target position. The operation is repeated for each screw. If the user misses one screw the computer display shows which screw must be readjusted until the final position of the guide matches the target. For instance, the screw that has the most important number of turns to be accomplished is suggested to the user. Or the screw are always adjusted in the same order, starting by screw 1, then 2, until screw N and the process is iterated by skipping screws that already reached the target position with a predefined limit.

Automatic Detection of the Screw ID

Advantageously, the device comprises detection means for determining the identification of the screw the tip is in contact with. Depending on the various embodiments disclosed below, each screw possesses within the navigation system identification (ID) means to distinguish it from the others.

In one preferred embodiment, illustrated on FIG. 3, the device detects which screw the tip is in contact with by a mechanical solution. To that end, a thin rigid mechanical stem 50 is sliding inside the device stem 41. By using the rigid mechanical link between the stem 50, the body 54, and the position cursor 51, the contact between the sliding stem 50 and the screw's head cavity 131 determines the value of the position sensor 52. When the tip is not inserted into the screw's head 130, a spring 53 places the position sensor 52 at its default position. When the tip is in the screw's head 130, the position sensor 52 measures the depth d of the screw's head cavity 131. This depth is measured and transmitted to the navigation system 2 by the wireless communication. Each screw's head cavity 131 has a different depth d, so that the position sensor delivers a different value for each screw, allowing the navigation system to know which screw the device is about to activate.

Figure 4:
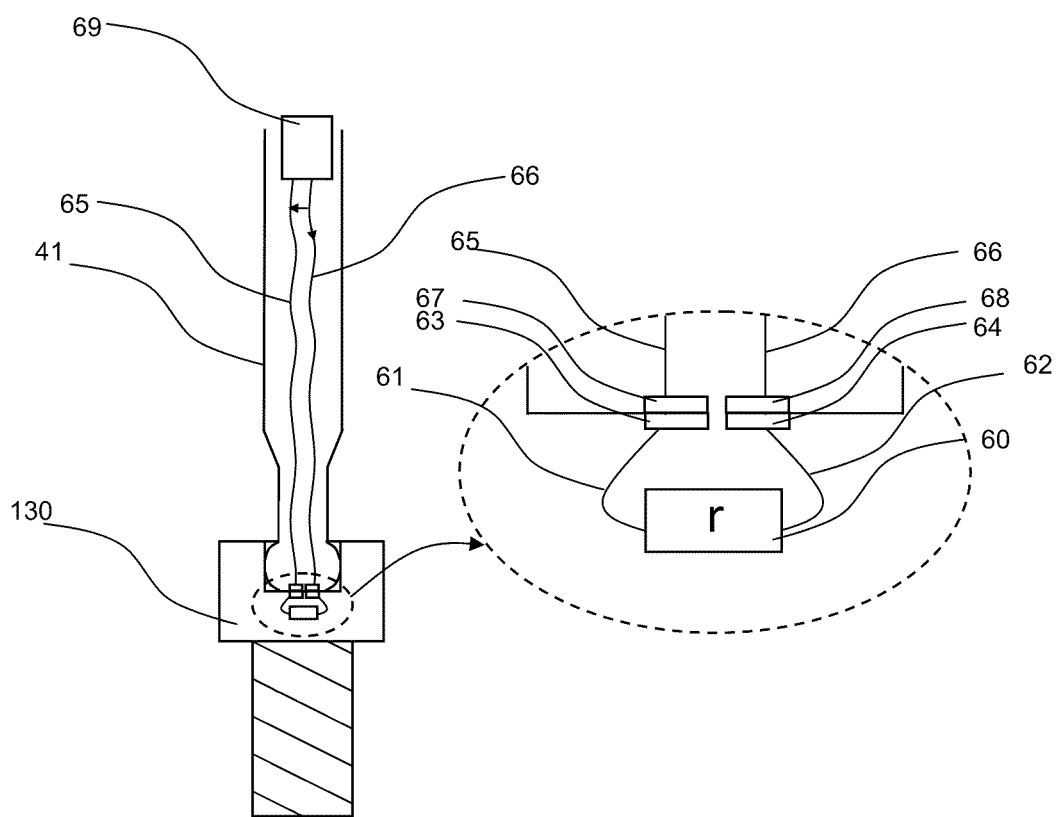
FIG. 4 is a partial sectional view of the Device stem, Device tip, and Instrument Screws, where the auto-detection of the screw is done by an electrical solution.

In another embodiment, illustrated on FIG. 4, the device detects which screw the tip is in contact with by an electrical solution. In this case, a resistance 60 is inserted into the screw's head 130 linked by two electrical wires 61, 62 respectively to two connectors 63, 64 that are on the bottom surface of the screw's head. In the device stem and tip are inserted two electrical wires 65, 66 that are respectively connected to two connectors 67 and 68 that are on the extremity of the device tip. When the tip is in the screw's head 130, the connectors 63 and 67 are in contact, as well as the connectors 64 and 68. It allows the device to measure the tension thanks to an ohmmeter 69. This tension is measured and transmitted to the navigation system by the wireless communication. Each screw's head has a different resistance value r, so that the ohmmeter 69 delivers a different value for each screw, allowing the navigation system to know which screw the device is about to activate.

Figure 5:
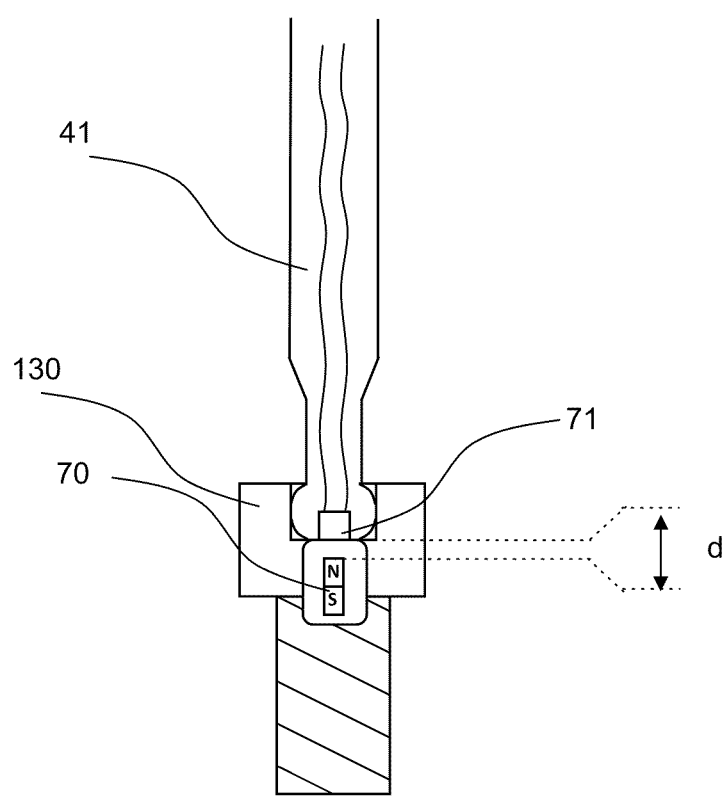
FIG. 5 is a partial sectional view of the Device stem, Device tip, and Instrument Screws, where the auto-detection of the screw is done by a magnetic solution.

In another embodiment, shown on FIG. 5, the device detects which screw the tip is in contact with by a magnetic solution. A magnet 70 is inserted into the screw's head 130. A "Hall effect" sensor 71 is inserted into the device tip that delivers a tension that is dependent of the distance between the magnet 70 and the sensor 71. This tension is measured and transmitted to the navigation system by the wireless communication. Each screw's head has the same magnet but inserted at a different depth d, so that the sensor 71 delivers a different tension for each screw, allowing the navigation system to know which screw the device is about to activate.

Figure 6:
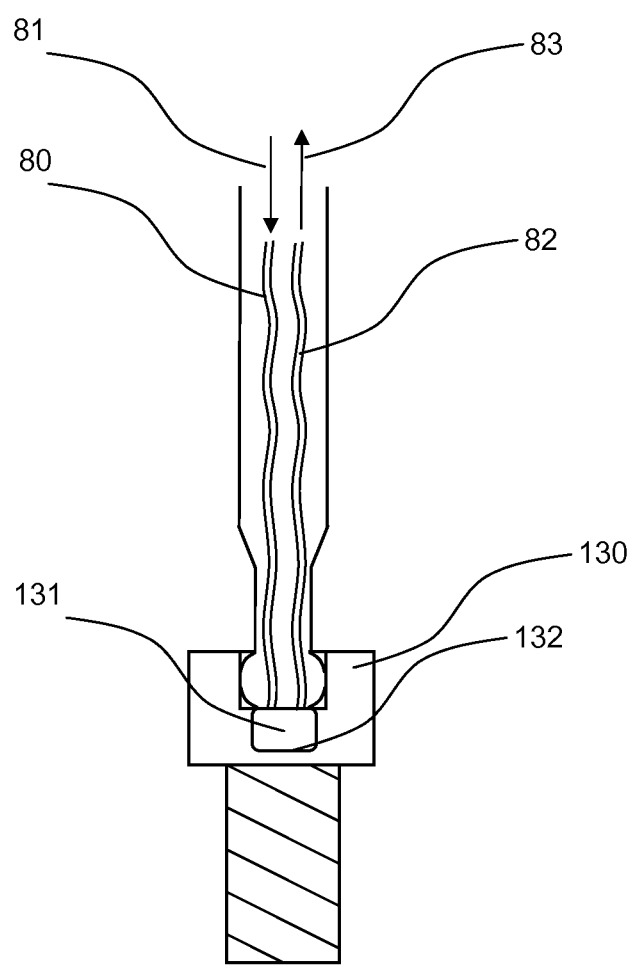
FIG. 6 is a partial sectional view of the Device stem, Device tip, and Instrument Screws, where the auto-detection of the screw is done by an optical solution.

In another embodiment, illustrated on FIG. 6, the device detects which screw the tip is in contact with by an optical solution. To that end, a cavity 131 is inserted into the screw's head 130. The bottom 132 of the cavity 131 is painted with a uniform color or with a pattern such as a bar code. A first optical fiber 80 carries light 81 from the device stem to the cavity 131, in order to light the cavity 131. A second optical fiber 82 carries the light 83 from the cavity to the device stem and then to an optical sensor such as a micro camera (not shown). The image delivered by the second optical fiber 82 is transmitted to the navigation system by the wireless communication. Each bottom 132 of screw's head cavity 131 has a different color or different pattern, allowing the navigation system to know which screw the device is about to activate.

Figure 7:
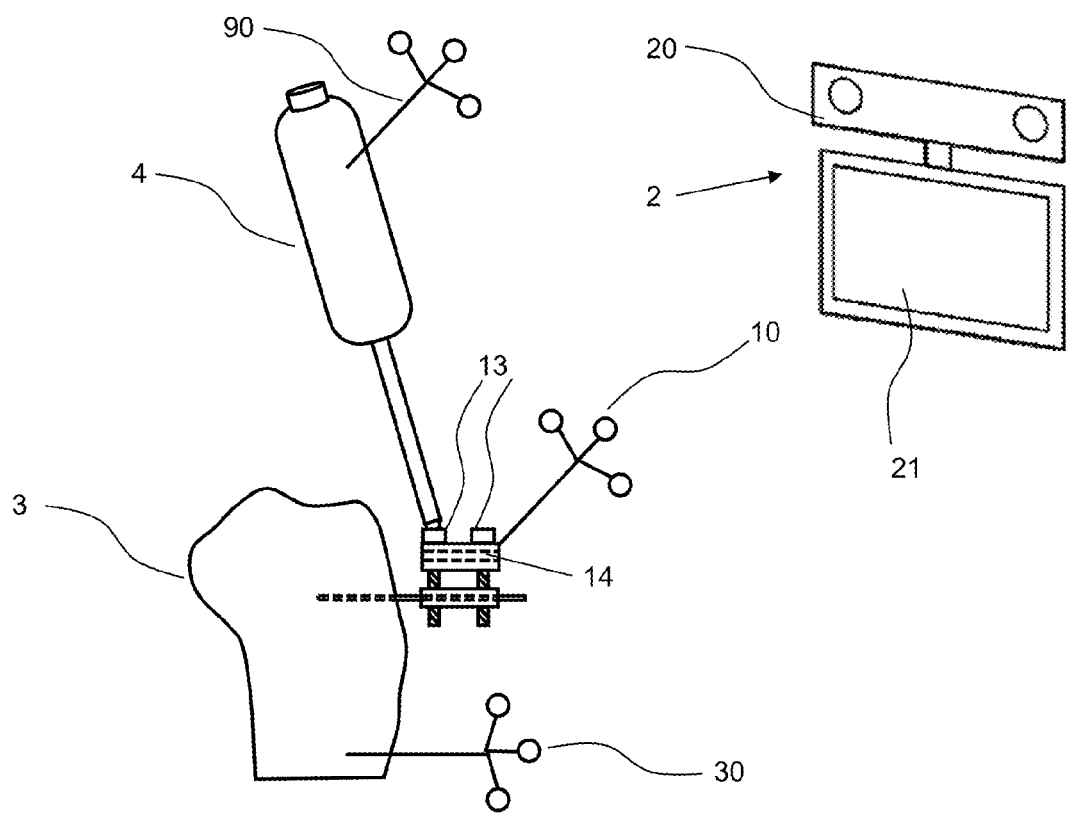
FIG. 7 is a sequential view of the Device, the navigation system, and the Instrument, where the auto-detection of the screw is done by a tracking solution.

In another embodiment, shown on FIG. 7, the device detects which screw the tip is in contact with by a tracking solution. A tracker 90 is rigidly fixed to the device 4. One knows by design the device tip position in the device tracker 90 coordinates system. One knows by design the screw's head position in the instrument tracker 10 coordinates system. Then, once the device tip is inserted into a screw's head, the navigation system 2 can determine which screw's head the device tip is inserted in, allowing the navigation system to know which screw the device is about to activate. If the accuracy of the navigation system is not sufficient, it can be compensated by adding a simple mechanical contact sensor that detects that the tip is in contact with the screw head.

In another embodiment (not illustrated here), the device detects which screw the tip is in contact with by a software solution: before the device activation, the navigation system records the position of the Instrument, called the initial position. When the user presses the activation button, the device turns as first step the stem in a constant known direction (e.g. clockwise). The navigation system then tracks the movement of the mobile part of the Instrument. By taking into account the design of the screw, the design of the Instrument, the given rotation direction and the number of turns that were applied, one can determine the unique screw that brought the instrument to this current position. Then, once the screw ID is determined by this first stem actuation, the device can then rotate the stem in the correct rotation direction with the correct number of turns to reach the target position.

Parallel Architecture

Figure 8:
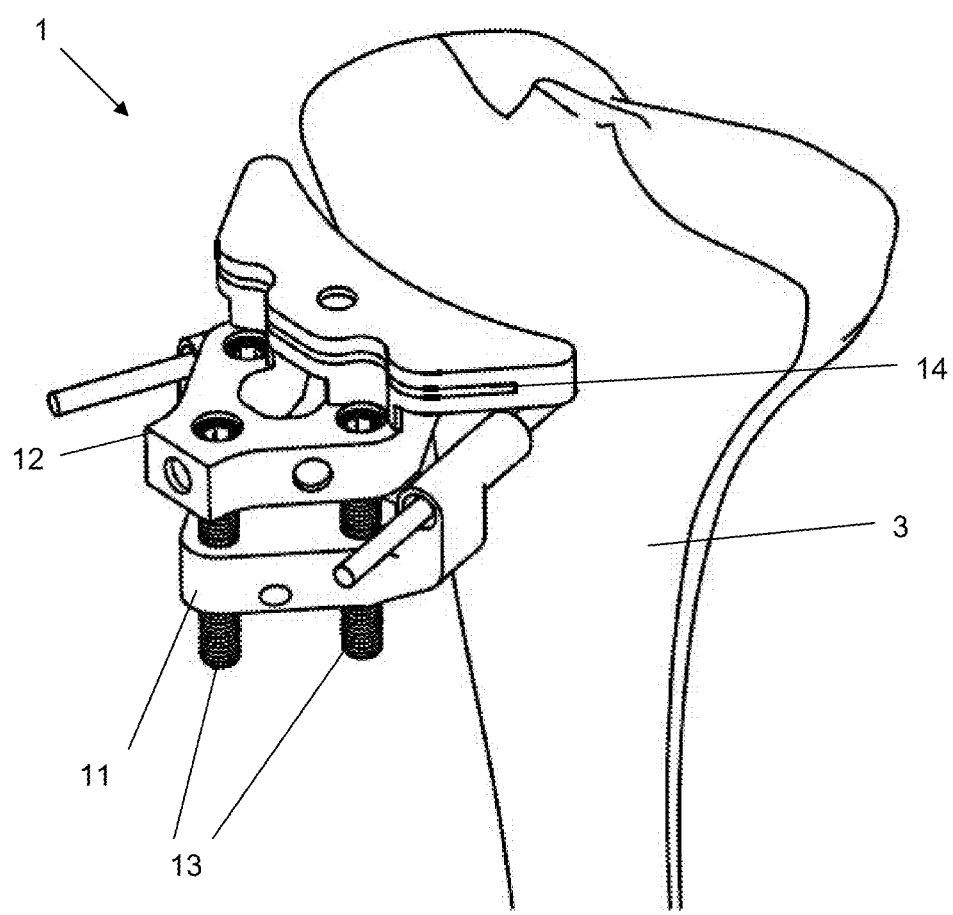
FIG. 8 illustrates a cutting slot which is adjusted by three screws assembled in a parallel architecture with respect with the basis fixed to the tibial bone.

In one preferred embodiment, illustrated on FIG. 8, the device is an adjustable cutting block for bone cuts with a parallel mechanical architecture made of three screws 13 between the fixed part 11 and the mobile part 12. To allow for various orientations of the cutting plane 14, at least two screws 13 have some small translational degrees of freedom parallel to the cutting plane at the level of their insertion in the block 12. It is also possible to add small ball-and-socket joints to add more flexibility to the device. This architecture is not reversible since a normal force applied to the mobile part does not move it. Therefore, with well manufactured mechanical components with high level of tolerance, the device is very stable except small motions in the plane which do not affect the accuracy of eth plane itself. In most cases, it is not necessary to fix the mobile part to the bone before making a cut using cutting plane 14.

Surgical Procedure Flow Diagram

Figure 9:
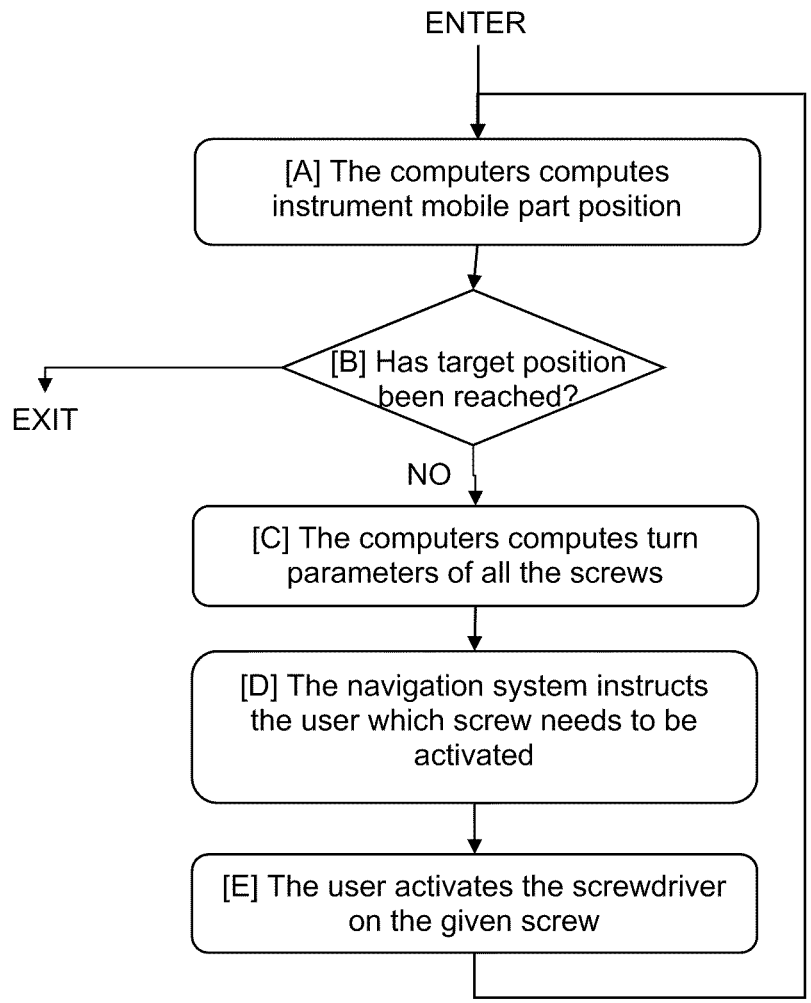
FIG. 9 is a surgical procedure flow diagram, showing how the surgeon is supposed to interact with the navigation system to adjust the desired instrument position.

The surgical procedure flow diagram is composed of steps [A], [B], [C], [D] and [E] that are described in FIG. 9.

[A] The computer 21 computes the current position of the instrument mobile part 12 with respect to the solid 3 thanks to the instrument tracker 10, the solid tracker 30, and the localizer system (14)

[B] If the current position is the target position then the procedure exits.

[C] If the target position is not reached, then for each screw 13i, where i is equal to 1, 2 or 3, the computer computes the unique number of turns Ti that needs to be applied on 13i, so that the mobile part 12 reaches the target position. Ti is positive if the rotation direction is clockwise and negative if the rotation direction is counter-clockwise. For that computation, the computers needs to know the target position of the instrument, which is selected by the surgeon, the screws parameters (diameter, thread length, thread thickness), which are known by design, the screws positions on the Instrument, which are known by design.

[D] The navigation system instructs the user which screw needs to be activated:
  i. In one preferred embodiment, the user is instructed to place the device tip 42 on a given screw's head. The computer displays on the screen which screw's head the device tip 42 must be placed on. In one preferred embodiment, each screw's head has a unique color, and the computer displays the color of the screw on the screen. In another embodiment, each screw's head is labeled with a unique number (such as 1, 2, 3), and the computer displays the number of the screw on the screen. In another embodiment, each screw's head is labeled with a unique letter (such as A, B, C), and the computer displays the letter of the screw on the screen. Screws can be also differentiated simply by their position on the instrument or by their shape. The user needs to follow the screws order displayed by the computer.
  ii. In another preferred embodiment, the user is instructed to place the device tip 42 on a given screw's head. Each screw's head has a unique characteristic such as color, or number, or letter as detailed in (i). The computer computes on which screw's head the device tip 42 must be placed on. The information is then transferred from the computer to the device by the wireless communication protocol. The device then instructs the user by displaying the information on itself, preferably on the top of the handle of the screwdriver. It can be by lighting some colored LEDs if screws are identified by a color, by lighting a letter if screws are identified by a letter, or by lighting a number if screws are identified by a number. The user needs to follow the screws order displayed by the computer or displayed on the handle of the screwdriver.
  iii. In another preferred embodiment, the user is not instructed to place the device tip 42 on a particular screw's head. The user can independently choose any screw's head, whatever the order is. The device detects when the tip is in contact or not of the screw's head, and detects which screw it is in contact with, and communicates the screw ID to the navigation system by the wireless communication protocol such that the adjustment necessary for that particular screw is known.

[E] Then the user presses the button 43 to activate the device. If the device is used with automated detection of contact and identification of screw head, pressing a button is not necessary and the device is activated automatically. The device stem 41 then turns the given number of turns Ti that was determined by the computer to reach the target position of the instrument. Once the device stem 41 has turned the desired number of turns Ti, the stem rotation stops, instructing the user that the target position for the screw 13i has been reached. Optionally, the navigation system 2 can check that the mobile part 12 has reached the desired position for that particular screw and if it is not the case, send an updated command to the screwdriver to add more portions of turn in order to adjust it accordingly and this process can be repeated until the position of the mobile part 12 has reached the desired position within a given arbitrary accuracy such as 0.2 mm for instance, which is done like a standard servoing mechanism. Then the instrument position is updated and the process goes to step [A] for setting other screws to the desired positions. The global process is iterated until all screws have reached their desired position such that the mobile part is now in its final target position for all desired degrees of freedom.

To reach a target screw position, there exists many possible methods to control the motors to optimize the speed of the process:

A first method consists in measuring the position of the mobile part before the screw has reached its final position using the navigation system and iterating the command on the motors that takes into account the measured position and the target position. Standard control commands can be used to optimize the speed and convergence of such process, for instance using well known Proportional Integral Derivative (PID) commands.

Another method consists in turning the motor in the right direction with an increasing speed and then decreasing speed when the motors come close to the expected position and finally stopping the motor when it has a very low speed so that the measurement taken with the navigation system can be done with averaging to reinforce accuracy and the time delay to stop the device is compliant because of low speed.

There exists many additional ways of optimizing the command by using the measurements of the final position of the mobile part using navigation system or by using the measurements of the motor controller that often provide the number of turns performed by the motor, with a division of such number by mechanical reduction. It is also possible to combine both measurements in real time in order to optimize and stabilize the convergence towards the target position.

ADVANTAGES OF THE INVENTION

The main advantage of the invention is to save intraoperative time. In a preferred embodiment the application is the adjustment of femoral distal cutting block and tibial cutting block for total knee replacement procedures. The conventional method with or without the use of a navigation system for aligning a cutting block is to use a set of several mechanical instruments, and to follow many steps that involve a lot of different mechanical instruments, which requires several minutes. The use of the invention reduces this operative time to a few seconds.

A second advantage is that the adjustment of the cutting block is automated and the user does not need to manage and think to complex iterations of several adjustments.

The advantage of the parallel architecture with 3 screws according to the present invention is that it continuously locks to its position in a non reversible way. The drawback of this architecture could be that the screws are not easy to adjust to their target value. However, the use of a motorized screwdriver to adjust the screws to their final position makes it possible to get the maximal benefit from the parallel architecture.

The invention claimed is:

1. A device for adjusting a position of a mobile part of a surgical instrument with respect to a solid, tracked by a navigation system, wherein the surgical instrument comprises a fixed part that is rigidly fixed to the solid so as to be immobilized with respect to the solid and the mobile part that is attached to the fixed part by several screws, wherein a rotation of at least one screw about an axis of rotation thereof moves the mobile part with respect to the fixed part along said axis of rotation,
the device comprising:
a stem comprising a tip suited to a head of the screws, the stem having a longitudinal axis,
a motorized system to drive the stem in rotation about the longitudinal axis,
communication means with the navigation system, such that the navigation system is configured to transmit to the motorized system screw identification information comprising a number of turns to apply to the stem in a screwing or unscrewing direction to reach a target position of each screw,
wherein the screws do not contact the solid, and
the axis of rotation and the longitudinal axis are parallel when the tip of the stem is positioned in the head of the respective screw for rotation thereof.

2. The device of claim 1, further comprising detection means to identify which screw the tip of the device is in contact with, wherein the communication means of the device are configured to transmit the screw identification information to the navigation system according to a wireless protocol or a wired protocol.

3. The device of claim 2, wherein the detection means comprise a sliding stem adapted to slide inside the stem and a position sensor adapted to measure the displacement of the sliding stem with respect to the tip of the device.

4. The device of claim 2, wherein the detection means comprise electrical connectors arranged at the tip of the device and an ohmmeter.

5. The device of claim 2, wherein the detection means comprise a "Hall effect" sensor arranged in the tip of the device.

6. The device of claim 2, wherein the detection
means comprise an optical sensor, a first optical fiber and a second optical fiber, the first and second optical fibers being arranged inside the stem so as to respectively light a cavity of the screw head and bring a light reflected by the cavity to the optical sensor.

7. The device of claim 2, wherein the detection means comprises a tracker rigidly attached to the device so as to be immobilized with respect to the device.

8. A method of adjusting a position of a mobile part of a surgical instrument with respect to a solid, tracked by a navigation system, wherein the surgical instrument comprises a fixed part that is rigidly fixed to the solid so as to be immobilized with respect to the solid and the mobile part that is attached to the fixed part by screws, wherein a rotation of at least one screw about an axis of rotation thereof moves
the mobile part with respect to the fixed part along said axis of rotation, comprising the following steps:
determining the position of the mobile part of the surgical instrument with respect to the solid,
comparing the determined position with respect to a target position of the mobile part with respect to the solid,
if the determined position is different from the target position, computing,
for each screw of the surgical instrument, a number of turns to apply in a screwing or unscrewing direction in order to move the mobile part until reaching with respect to the fixed part to the target position of the mobile part,
providing a device, the device comprising:
a stem comprising a tip suited to a head of the screws, the stem having a longitudinal axis,
a motorized system to drive the stem in rotation about the longitudinal axis,
communication means with the navigation system, such that the navigation system is configured to transmit to the motorized system the number of turns to apply to the stem in a screwing direction to reach a target position of each screw,
for each screw, positioning the tip of the stem of the device in the respective screw head such that the longitudinal axis of the stem is parallel to the axis of rotation of the screw,
operating the motorized system of the device such that it rotates
the stem about the longitudinal axis the computed number of turns in a screwing or unscrewing direction,
wherein the fixed part is immobilized before applying to the stem the computed number of turns in a screwing or unscrewing direction.

9. The method of claim 8, wherein the solid is a tibia or a femur, the surgical instrument is a cutting block with a cutting plane and three screws assembled in a parallel architecture are used for adjustment of the plane.

10. A computer assisted surgical navigation system for adjusting a position of a mobile part of a surgical instrument with respect to a solid, wherein the surgical instrument comprises a fixed part that is rigidly fixed to the solid so as to be immobilized with respect to the solid and the mobile part that is attached to the fixed parts by screws, wherein a rotation of at least one screw about an axis of rotation thereof moves the mobile part with respect to the fixed part along said axis of rotation, the surgical navigation system comprising:

a first reference element applied to the solid that generates a first three-dimensional dynamic reference tracker, which is independently registered in the surgical navigation system, a second reference element applied to the mobile part of the surgical instrument that needs to be adjusted, that generates a second three-dimensional dynamic reference tracker, which is independently registered in the surgical navigation system, a computer, and a device, the device comprising:

a stem comprising a tip suited to a head of the screws, the head having a longitudinal axis, a motorized system to drive the stem in rotation about the longitudinal axis, communication means with computer, such that computer is configured to transmit to the motorized system a number of turns to apply to the stem in a screwing or unscrewing direction to reach a target position of the each screw, wherein the computer is configured to determine the number of turns to be applied to the each screw by the stem of the device and the screwing or unscrewing direction for the each screw, taking into account a position of the mobile part determined by the second reference element, a target position of the mobile part, the geometry of the screws and the geometry of the surgical instrument, and to transmit to the device by the communication means the determined number of turns to be applied.

11. The device of claim 1, wherein the device further comprises a body, wherein the motorized system rotates the stem with respect to the body.

12. The device of claim 2, wherein the navigation system comprises identification means to distinguish the each screw.

13. The method of claim 8, further comprising identifying which screw the tip of the device is in contact with.

14. The device of claim 1, wherein the device further comprises a button configured to be activated by a user.

15. The method of claim 8, wherein the screws do not contact the solid.

16. The method of claim 8, further comprising determining a second position of the mobile part of the surgical instrument with respect to the solid after some of the computed number of turns are applied, comparing the second determined position with respect to a target position of the mobile part with respect to the solid, if the second determined position is different from the target position, computing, for each screw of the surgical instrument, a second number of turns to apply in a screwing or unscrewing direction in order to move the mobile part with respect to the fixed part to the target position of the mobile part, for each screw, positioning the tip of the stem of the device in the respective screw head such that the longitudinal axis of the stem is parallel to the axis of rotation of the screw, and operating the motorized system of the device such that it rotates the stem the second computed number of turns in a screwing or unscrewing direction.

17. The method of claim 8, wherein operating the motorized system of the device such that it applies to the stem the computed number of turns in a screwing or unscrewing direction comprises operating the motorized system at a first speed and operating the motorized system at a second speed less than the first speed when the position of the mobile part is near the target position.

18. The device of claim 1, wherein the screws are not directed towards the solid.

19. The device of claim 1, wherein at least an end portion of the tip is constructed for insertion into a recess in the head of the respective screw, the head of each screw is disposed at an axial end of the screw, and the head of each screw is positioned on an exterior of the surgical instrument so as to be accessible by said end portion of the tip.

20. The method of claim 8, wherein the positioning the tip of the stem in the respective screw head comprises inserting at least an end portion of the tip into a recess in the head of the respective screw, the head of each screw being disposed at an axial end of the screw, and the head of each screw is positioned on an exterior of the surgical instruction so as to be accessible by said end portion of the tip.

21. The system of claim 10, wherein at least an end portion of the tip is constructed for insertion into a recess in the head of the respective screw, the head of each screw is disposed at an axial end of the screw, and the head of each screw is positioned on an exterior of the surgical instrument so as to be accessible by said end portion of the tip.

* * * * *